(12) United States Patent
DeToro et al.

(10) Patent No.: US 6,377,178 B1
(45) Date of Patent: Apr. 23, 2002

(54) THERAPEUTIC ANKLE & FOOT APPARATUS HAVING A CONTACT SENSOR MECHANISM

(75) Inventors: William DeToro, 3409 Olde Winter Trail, Poland, OH (US) 44514; Brian Perala, Geneva, OH (US)

(73) Assignee: William DeToro, Poland, OH (US)

( * ) Notice: Subject to any disclaimer, the term of this patent is extended or adjusted under 35 U.S.C. 154(b) by 0 days.

(21) Appl. No.: 09/597,027

(22) Filed: Jun. 20, 2000

(51) Int. Cl.$^7$ .............................................. G08B 23/00
(52) U.S. Cl. ...................... 340/573.1; 340/575; 602/19; 602/23
(58) Field of Search .......................... 340/573.1, 573.7, 340/575, 576, 598, 593, 626, 665, 666, 686.1, 825.19; 2/44, 45; 602/19, 23, 26, 27

(56) References Cited

U.S. PATENT DOCUMENTS

| | | | | |
|---|---|---|---|---|
| 491,271 A | * | 2/1893 | Rowley ........................ | 602/23 |
| 612,087 A | * | 10/1898 | Boyd ........................... | 602/23 |
| 4,647,918 A | | 3/1987 | Goforth | |
| 4,760,850 A | * | 8/1988 | Phillips et al. ................ | 607/49 |
| 4,807,640 A | * | 2/1989 | Watson et al. .............. | 340/575 |
| 5,135,471 A | * | 8/1992 | Houswerth ................... | 601/19 |
| 5,253,654 A | * | 10/1993 | Thomas et al. ............. | 128/779 |
| 5,431,624 A | * | 7/1995 | Saxton et al. ................. | 602/27 |
| 5,500,635 A | * | 3/1996 | Mott ........................... | 340/693 |
| 5,566,479 A | | 10/1996 | Gray et al. | |
| 5,593,383 A | * | 1/1997 | DeToro ....................... | 602/27 |
| 5,599,287 A | * | 2/1997 | Beczak, Sr. et al. .......... | 602/19 |
| 5,632,724 A | * | 5/1997 | Lerman et al. ............... | 602/19 |
| 5,642,096 A | | 6/1997 | Leyerer et al. | |
| 5,678,448 A | | 10/1997 | Fullen et al. | |
| 5,833,639 A | * | 11/1998 | Nunes et al. .................. | 602/23 |
| 5,877,687 A | * | 3/1999 | Bernard et al. ............. | 340/573 |
| 6,010,472 A | * | 1/2000 | Schiller ....................... | 602/19 |
| 6,031,463 A | * | 2/2000 | Bechmann .................. | 340/573 |
| 6,056,712 A | * | 5/2000 | Grim ........................... | 602/27 |
| 6,090,059 A | * | 7/2000 | Wasserman et al. .......... | 602/27 |
| 6,228,044 B1 | * | 5/2001 | Jensen et al. ................. | 602/27 |

\* cited by examiner

*Primary Examiner*—John A. Tweel
(74) *Attorney, Agent, or Firm*—Harpman & Harpman

(57) ABSTRACT

A therapeutic ankle and foot apparatus having a contact sensor mechanism. The sensor mechanism comprising a contact switch disposed between an ankle and foot apparatus and the heel of a patient's foot. The contact sensor mechanism determines any proximal contact with the patient's heel and communicates with an activation indicator that contact is present. The activation indicator may be visual and/or audible, and it may be positioned on the apparatus or at a remote location, communicating by wire or wireless telecommunication linkage.

31 Claims, 8 Drawing Sheets

THERAPEUTIC ANKLE & FOOT APPARATUS HAVING A CONTACT SENSOR MECHANISM

BACKGROUND OF THE INVENTION

1. Technical Field

This invention relates to orthotic and prosthetics that have sensor devices used to continuously monitor the amount of pressure on soft tissue confined therein. Orthosis such as therapeutic ankle and foot brace support the patient's foot for isolated pressure relief against portions thereof. Optimal outcome for such processes are jeopardized by improper refitting of the orthotics by the patient or unskilled caregiver.

2. Description of Prior Art

Prior art devices of this type have generally been directed to pressure sensing devices that measure the effective pressure on the patient's foot with the supporting surfaces. Typically, such pressure sensing devices are integrated within the footwear such as shoes as seen in U.S. Pat. Nos. 4,647,918, 5,566,479, 5,642,096 and 5,678,448.

In U.S. Pat. No. 4,647,918 a multiple event pressure notification system is disclosed wherein multiple pressure monitoring points are arranged within the footwear and interconnected to a microprocessor programmed to detect varying pressure amounts and calculate same to time and locale. An alarm sounds when pressure exceeds a pre-programmed threshold at any one of the given pressure indicating points.

U.S. Pat. No. 5,566,479 discloses a shoe for diabetics or others having four sensor resistors that activate an alarm circuit when a pre-selected threshold pressure amounts are reached.

U.S. Pat. No. 5,642,096 uses a series of pizorisistois sensors arranged in arrayed pairs within the inner sole of the footwear in pressure increase and decrease arrays. The system measures both pressure and temperature through which the patient's foot is exposed.

U.S. Pat. No. 5,678,448 defines a self-contained system to measure forces that are applied to the foot within the shoe by a matrix of four sensors covering the inner sole of the shoe.

Additional prior art is directed to pressure sensing systems to measure increasing pressure between the injured portion of a patient's body and confinement, see, for example, U.S. Pat. No. 4,858,620 having a plurality of pressure sensors within an orthopedic restraining member that indicates once a critical pressure value is reached an alarm activation.

U.S. Pat. No. 5,790,256 is directed to a foot analyzer that uses both pressure sensing and optical sensors to analyze a patient's foot placed within the sensing enclosure.

Finally, U.S. Pat. No. 5,838,214 refers to an interface pressure measurement device that interfaces between a patient's foot and surrounding support surfaces. The device has two sensor sheets of thin flexible plastic material arranged so that when the sheets touch an electrical contact is presented forming a sensing switch.

SUMMARY OF THE INVENTION

A therapeutic ankle and foot apparatus having a contact sensor indicator whereby any physical pressure on the isolated portion of the patient's foot will be detected and indicated by an auditory and visual activation alarm circuit. The contact sensor can be one of a variety of pressure or proximal activation switching elements positioned between the patient's foot and the therapeutic ankle and foot apparatus.

DESCRIPTION OF THE PREFERRED EMBODIMENT

Figure 1:
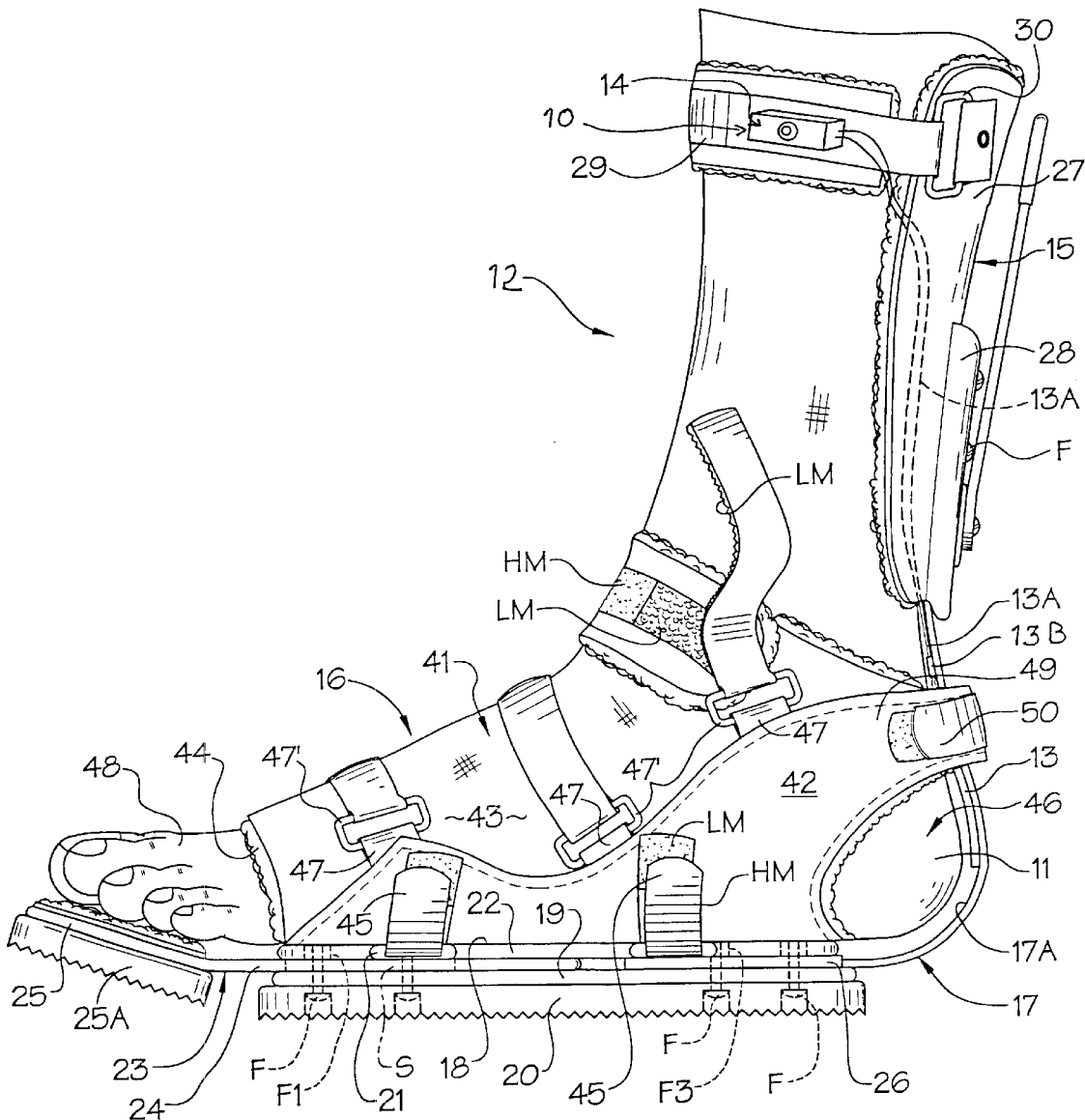
FIG. 1 is a side elevational view of the therapeutic ankle and foot brace with the contact sensor indicator positioned therein.

A contact sensor mechanism 10 can be seen in FIGS. 1–5 of the drawings to detect any contact of a patient's heel 11 within an ankle and foot apparatus 12. The contact sensor mechanism 10 has a contact switch 13 and interconnected by wires 13A to an activation indicator 14.

The ankle and foot apparatus 12, best seen in FIG. 1 of the drawings, has a leg portion 15 and a foot portion 16 and a heel portion 17. The foot portion 16 is at an angle to the leg portion 15 interconnected by the heel portion 17. The foot portion 16 has a footpad 18 connected to an attachment base 19. A resilient walking pad 20 is secured to the attachment base 19. A pair of longitudinally spaced aperture tabs extend from the respective side edges 22 of the footpad 18. A toe support extension member 23 adjustably extends from the foot portion 16. The toe support extension member 23 has a generally flat base area 24 with an angularly offset end portion 25 with a resilient pad 25A secured thereto. The toe support extension member 23 is adjustably positioned between the footpad 18 and the attachment base 19 by a pair of fasteners F. The fasteners F extend through the apertures in the attachment base 19 and the resilient walking pad 20 via registration slots S shown in broken lines within the flat base area 24. The fasteners F are threadably secured into the respective fittings F1 within the footpad. It will be seen that the heel portion 17 extends from a mounting pocket 26 formed within the bottom of the footpad 18. The heel portion 17 is secured within the mounting pocket 26 by a pair of threaded fasteners F extending through respective apertures in the resilient walking pad 20 and attachment base 19 and are threadably secured into a fitting F3 in the footpad 18.

The heel portion 17 is transversely flat and longitudinally contoured extending from the foot portion 16 to and engageable within the leg portion 15 so as to provide a space between the patient's heel 11 and the heel portion 17.

The leg portion 15 has an enlarged transversely contoured leg support member 27 with a recessed channel 28 within. The heel portion 17 is secured within the recesses channel 28 by fasteners F as will be well understood by those skilled in the art.

Figure 2:
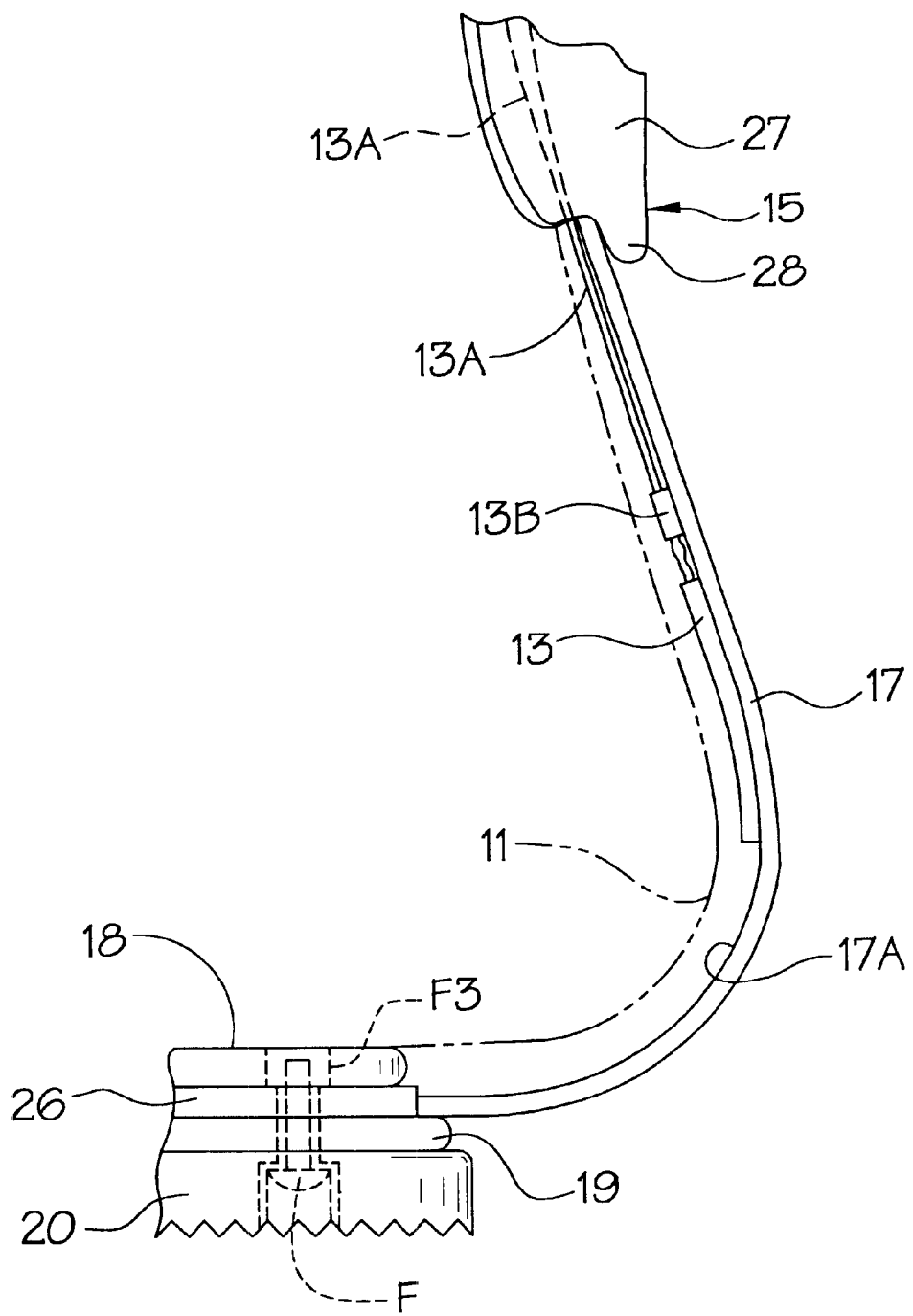
FIG. 2 is an enlarged partial side elevational view of the heel spacing portion of the brace illustrating switching elements of the invention positioned therein.
Figure 3:
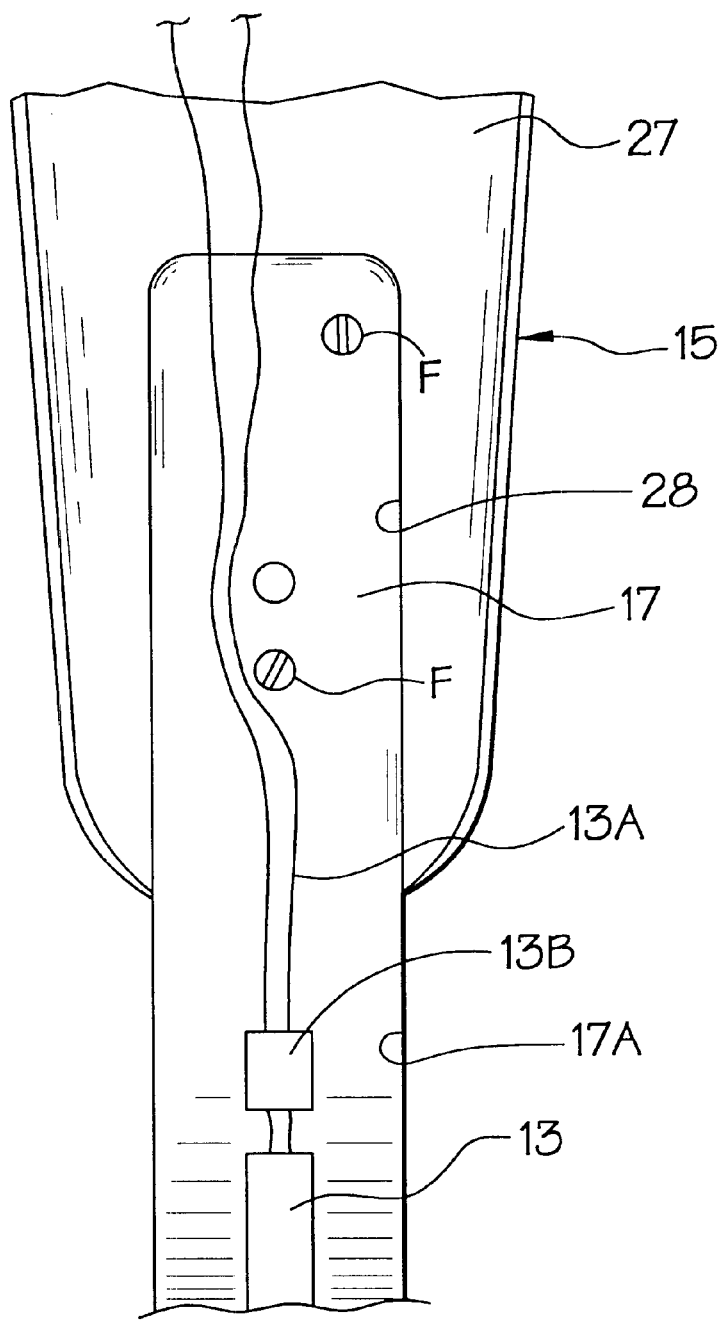
FIG. 3 is a partial front elevational view of a heel and leg support element of the brace with the switching elements of the invention secured thereto.

By referring to FIGS. 1–3 of the drawings, the contact sensor mechanism 10 can be seen having a contact switch 13, secured to an inner surface 17A of the heel portion 17 facing the patient's heel 11. Lead wires 13A extend from the contact switch 13 along the leg support member 27 and are interconnected to the activation indicator 14. In this embodiment, the activation indicator 14 is positioned on the leg engagement strap 29 that is adjustably secured to the leg support member 27 by buckles 30 as best shown in FIG. 1 of the drawings. It will be apparent to those knowledgeable within the art that different mounting positions for the activation indicator 14 can be utilized and it is a matter of choice as to the exact positioning of the activation indicator 14.

Referring to FIGS. 3–5 and 7 of the drawings, the contact switch 13 can be seen having a generally flat rectangular base member 31 with a plurality of longitudinally spaced annular recessed areas 32 therein. The rectangular base member 31 is preferably made of a non-conductive synthetic material. Each of the recess areas 32 has a contact wire 33 extending thereacross which are in communication with lead wires 33A which in turn communicate with one another forming one side of an electrical contact circuit. A resilient conductive thin metal mask 34 is bonded to a thin non-conductive carrier strip 35 and overlies the rectangular base 31. The conductive mask 34 defines multiple registration activation disks areas 34A aligned over the respective recess areas 32 in spaced relation thereto so as to form multiple deflectable contact switches 35A. Such contact switches are commercially referred to as ribbon or membrane activators for large area coverage and are available from a variety of commercial sources. It will be evident from the description above that other commercially available electrical switches of this type can be substituted having a low activation force and with a low to moderate height profile. An example of a preferred switch activation force requirement would be in the range of 50 to 100 grams of impingement force to deflect a switch portion providing a contact and activation of the same.

Figure 4:
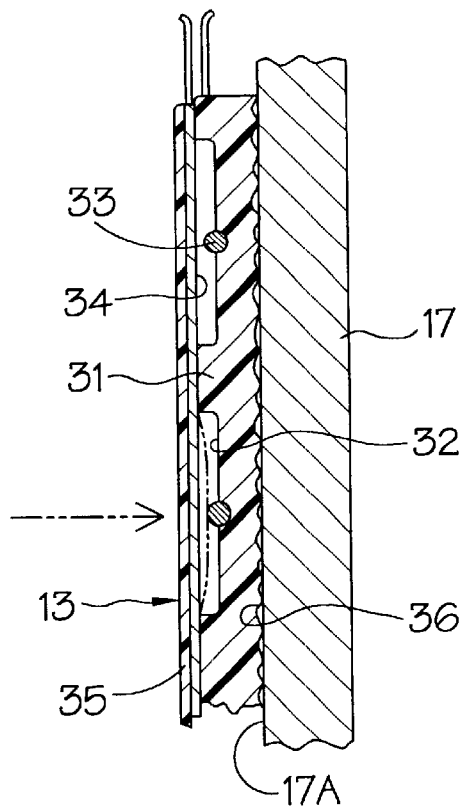
FIG. 4 is an enlarged partial cross-sectional view of the contact switch strip chosen for illustration representation.
Figure 5:
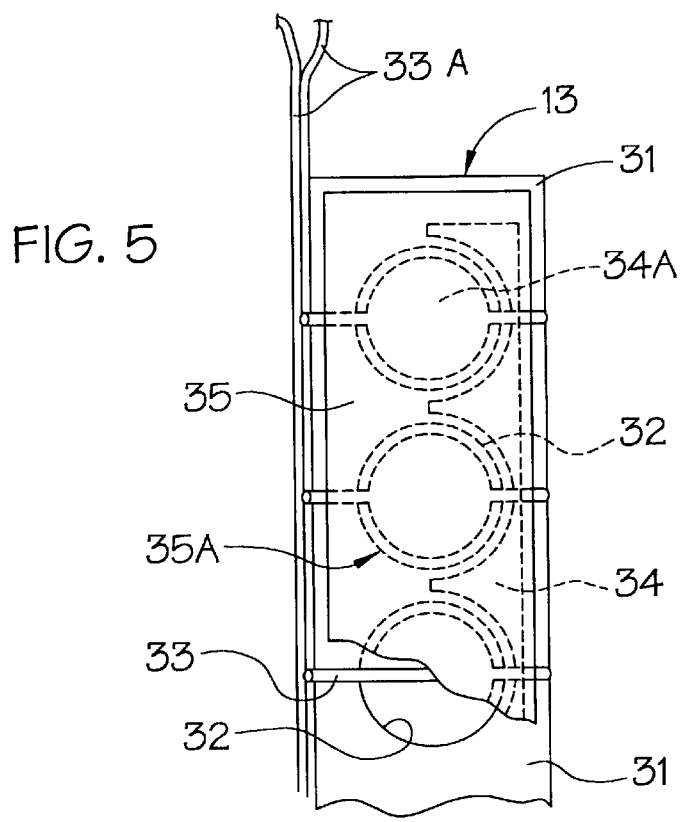
FIG. 5 is enlarged partial top plan view of the contact switch strip as seen in FIG. 4 with portions broken away.

It will be evident that the positioning of the contact switch 13, in this preferred embodiment on the heel portion 17 is critical to its effectiveness so that any contact of the patient's heel 11 or adjacent heel area 11A with the foot and ankle apparatus 12 can be detected so that the same can be readjusted to fit properly. The contact switch 13 therefore will be preferably positioned based on its physical characteristics and chosen method of mounting which in this example is an adhesive band 36 on the rectangular base 31, as seen in FIG. 4 of the drawings.

A proximal switch 13B is also illustrated in FIGS. 1, 2 and 3 of the drawings wherein a secondary switching device is used in conjunction with the primary contact switch 13 to afford additional warning of engagement by the patient's foot with the ankle and foot apparatus 12. The proximal switch 13B is also interconnected to the activation indicator 14 via the wires 13A.

Figure 7:
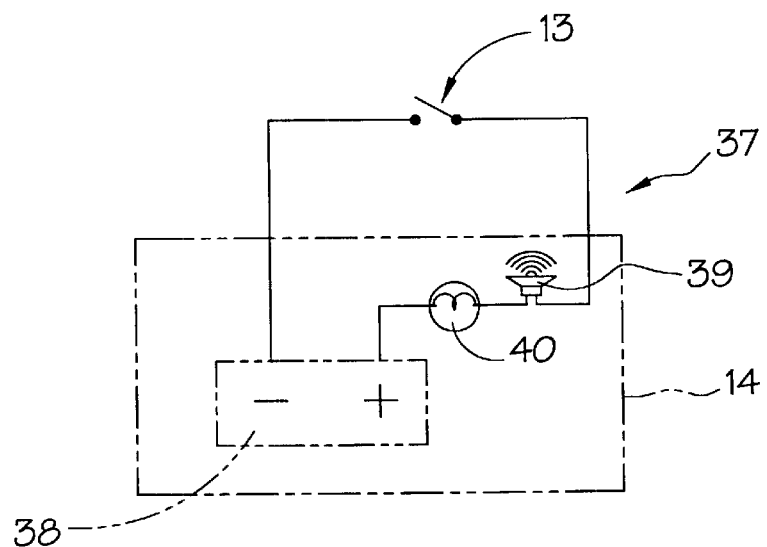
FIG. 7 is an illustrative circuit diagram of an alarm activation circuit associated with the invention.

Referring to FIG. 7 of the drawings, a system circuit 37 of the activation indicator 14 can be seen illustrated within the broken lines. The system circuit 37 comprises a source of power 38 (battery), an audible output device 39 and a visual warning light 40 and the contact switch 13. When the contact switch 13 is activated the circuit is completed which activates the visual and auditory circuit elements. It will be evident that either the warning light 40 or audible output device 39 can be used in accordance with the preference of the user's environment as will be well understood by those skilled in the art.

Referring again to FIG. 1 of the drawings, a fabric foot engagement enclosure 41 is shown having a durable mounting base portion 42 securing a fabric sleeve 43 that is lined with a soft synthetic fur-like material 44. The durable mounting base 42 provides a reinforcement contoured mounting surface from which a plurality of fastening straps 45 removably secure the foot engagement enclosure 41 to the foot pad 18. The straps 45 extend through the apertured tabs 21 holding the same in position thereagainst.

The fabric sleeve 43 and durable mounting base 42 define a cutout heel portion 46 for the patient's heel 11. Secondary straps 47 extend from the fabric sleeve 43 and the durable mounting base 42 for registered engagement through respective buckles 47' to secure the foot portion 16 about a patient's foot 48. Releaseably securing hook material HM and loop material LM, collectively referred to as releasable securing materials are used on the fastening straps 45 and secondary straps 47 for self-engagement through the respective buckles 47' and apertured tabs 21, securing the durable mounting base portion 42 to the base 18.

In use, the patient's foot 48 is positioned within the fabric foot engagement enclosure 16 and secondary straps 47 are secured through the respective buckles 47'. A pair of heel tabs 49 formed from the hereinbefore disclosed mounting base 42 and fabric sleeve 41 are secured in overlapping relationship over the patient's heel 11 by straps 50 which are the same releasable securing material LM and HM.

Figure 6:
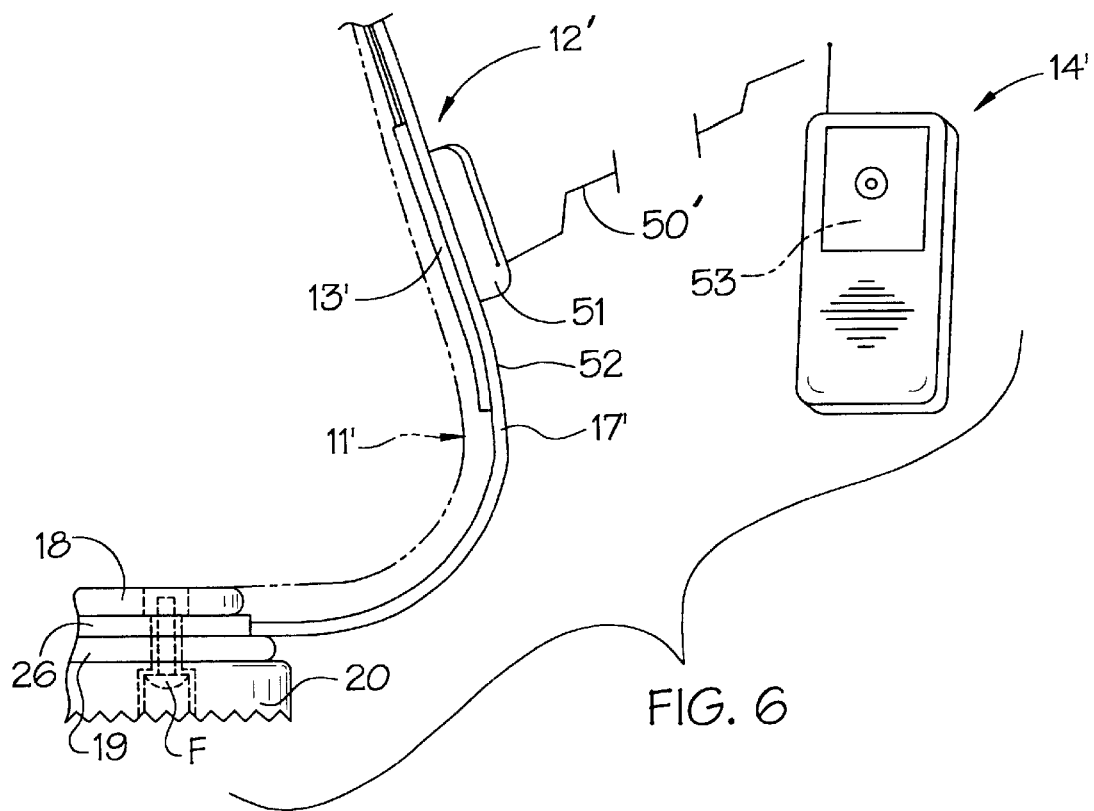
FIG. 6 is an illustrated side elevational view of an alternate form of the invention.

Referring now to FIG. 6 of the drawings, an alternate form of the invention is illustrated wherein a contact switch 13' is positioned on a heel portion 17' of an ankle and foot apparatus 12'. A self-contained wireless transmitter 51 is secured to the outer surface 52 of the heel portion 17' and in communication with the contact switch 13'. A remotely located alarm module 14' has a wireless receiver 53 therein for receiving an output signal 50' from the wireless transmitter 51 when it is activated through the patient's foot or heel contacting the switch 13' as hereinbefore described.

It will be evident from the above referred to description that should the patient's heel 11 or adjacent foot area contact the contact switches 13, 13' or 13B that the activation indicator 14 or 14' will activate indicating that adjustment needs to be made with the orthotic brace 12 or 12' to alleviate engagement pressure and possible tissue breakdown of the patient's affected area.

Figure 8:
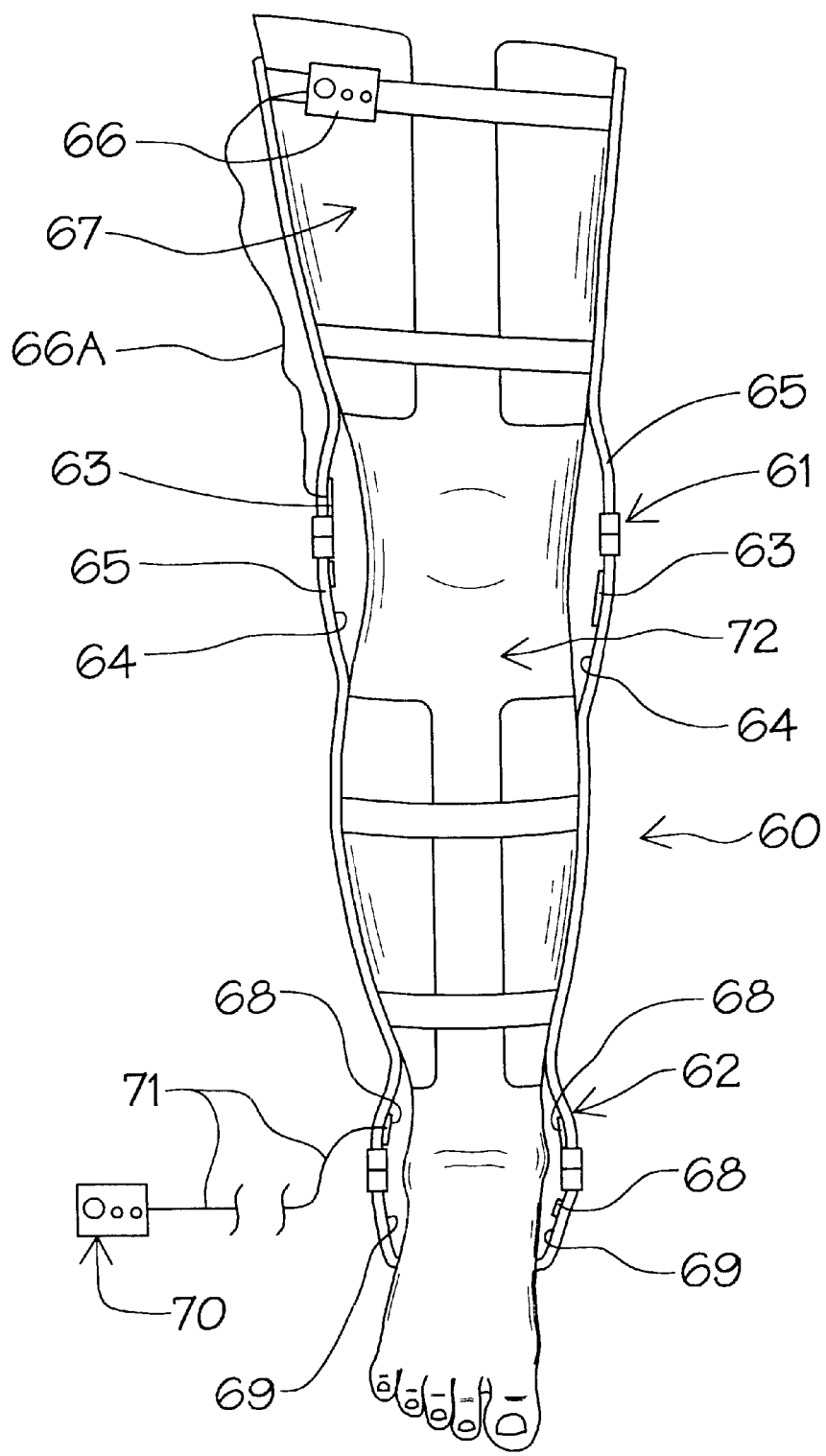
FIG. 8 is a front elevational view of an alternate form of the invention illustrating a sensor circuit of the invention on a leg brace.

Referring to FIG. 8 of the drawings, an alternate form of the invention can be seen wherein a leg brace 60 is illustrated having a knee joint portion 61 and an ankle joint portion 62 as will be well understood by those skilled in the art. The knee joint portion 61 of the leg brace 60 has a contact switch strip 63 as hereinbefore described (as contact switch 13) being secured adhesively to the inner side surface 64 of a joint brace armature 65.

An alarm activation indicator module 66 positioned on an upper portion 67 of the leg brace 60 and is interconnected by wires 66A to the respective contact switch strips 63. The alarm activation indicator 66 is identical to that of the activation indicator 14 as set forth in the preferred embodiment above.

Referring now to the ankle joint portion 62 of the leg brace 60, a sensor contact switch strip 68 is adhesively secured to an inner surface 69 of the ankle joint portion 62 and is interconnected to a remote alarm activation indicator 70 by quick release leads 71 (well known and understood by those skilled in the art).

Both the contact switch strip 63 and 68 respectively are positioned on brace areas that are required to maintain an air contact gap between the brace elements and a portion of the patient's leg 72.

Figure 9:
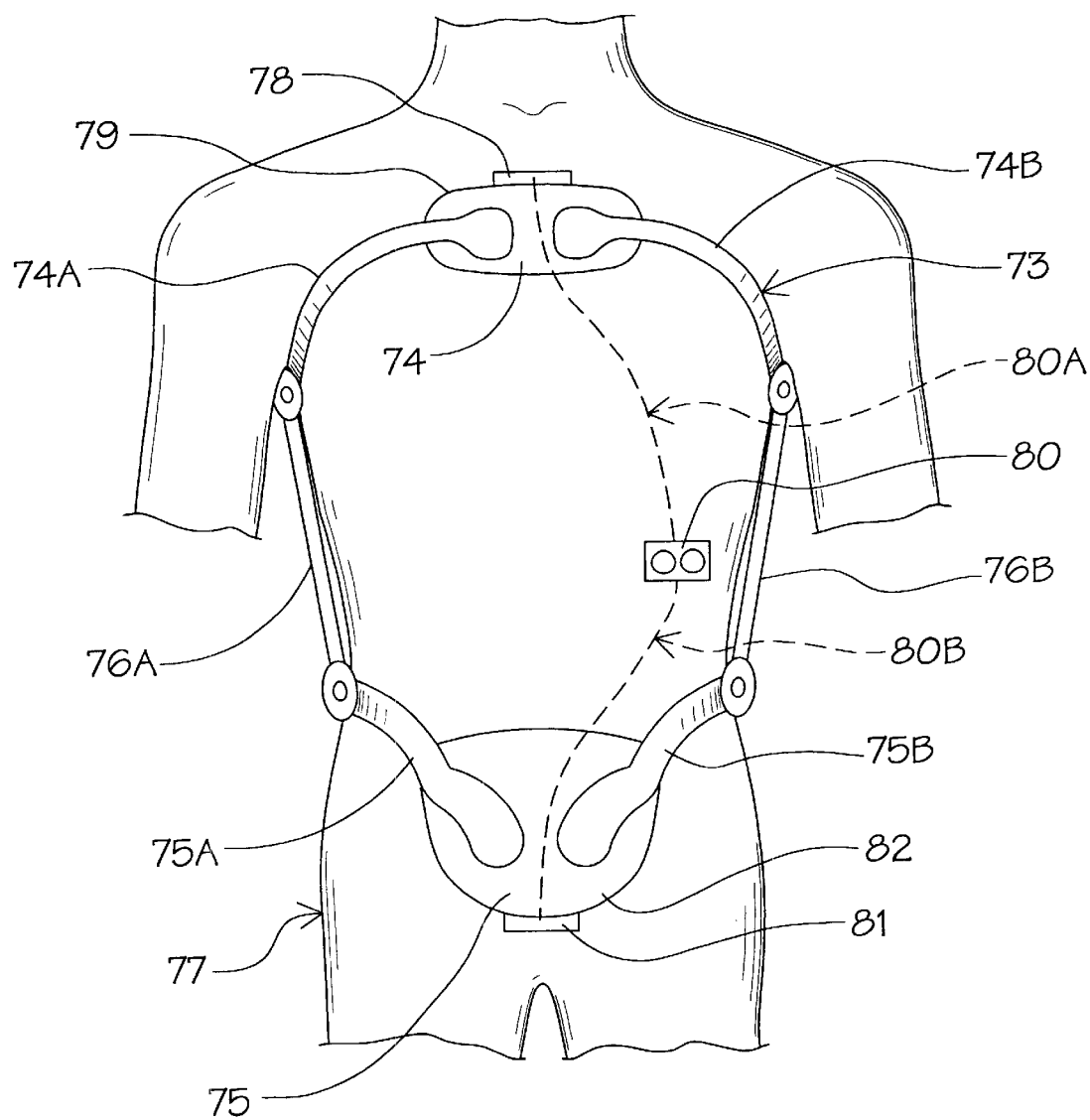
FIG. 9 is a front elevational view of a second alternate form of the invention illustrating an anterior hyper-extension brace with contact sensors positioned within.

Referring now to FIG. 9 of the drawings, an anterior hyper-extension body brace 73 can be seen having a sternum pad 74 and a pubic engagement brace pad 75, each with engaging arm pairs 74A & 74B and 75A & 75B extending therefrom and being interconnected by a pair of metalized brace elements 76A & 76B as is typical within the art. In many applications due to the impaired sensor perception of a disabled patient 77 it is important to maintain proper positioning of the brace 73 which given the human physiology will move during transition from a sitting position to a standing or laying position.

In order to detect such movement, a contact sensor switch 78 is positioned on the top edge 79 of the sternum pad 74 with a self-contained alarm activation indication module 80 interconnected by wires 80A.

Conversely, the pubic brace pad 75 has a contact sensor switch 81 as hereinbefore described positioned on its bottom perimeter edge 82 interconnected to the alarm activation indication module 80 by wires 80B. It will be evident that upon relative movement of the sternum pad or pubic pad in relation to the patient, the contact switch will activate the alarm activation module indicator alerting the patient and/or caregivers to the inappropriate positioning of the brace.

Figure 10:
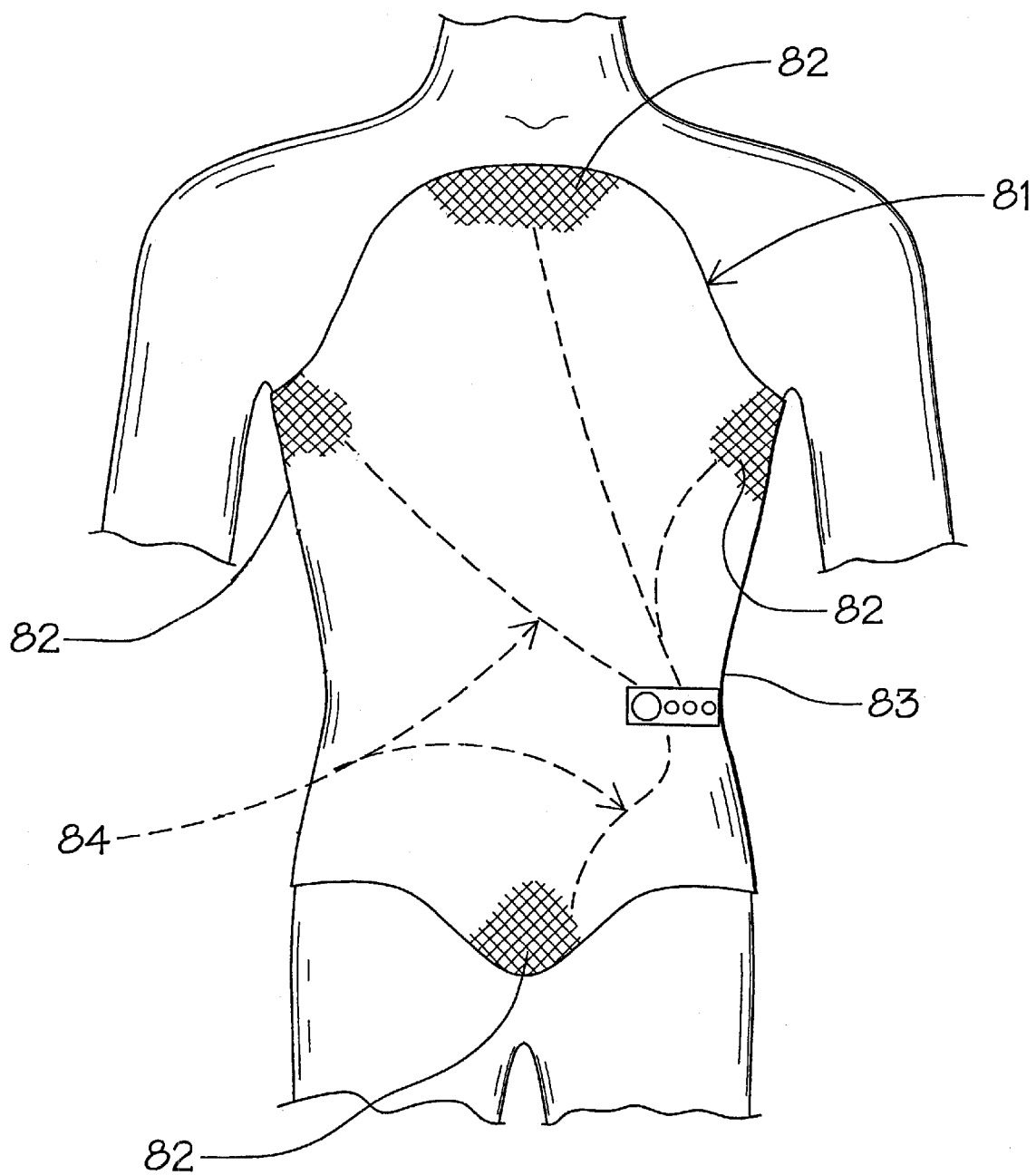
FIG. 10 is a front elevational view of a third alternate form of the invention illustrating a sensor circuit on a body jacket brace.

Referring now to FIG. 10 of the drawings, a modified therapeutic body jacket brace 81 can be seen which is used for therapeutic support and immobilization, again which is well known and typical within the art.

A plurality of thin contact sensor pads 82 indicated by shaded areas are integrally positioned on the inner surface of the body jacket brace 81 in specified non-contact areas. An alarm activation module indicator 83 is interconnected to the multiple contact sensor pads 82 by wired as indicated by dotted lines at 84. It will be evident that the alarm activation indicator module 82 is identical to the hereinbefore-described activation indicator 14 of the preferred embodiment and defines the system circuit 37 as noted above. Such system circuits 37 can be easily modified by those skilled in the art to support individual sensor activation indicators so that specific sensor activation can be determined as well as integrated sensor connection which any of the sensors will activate the central alarm activation indicator modules 82 upon contact.

Both the alternate contact sensor mechanisms illustrated and described in FIGS. 9 and 10 of the drawings can also be formatted as remote alarm activation indicator modules wherein the respective alarm activation indication modules 77 and 82 are remotely positioned from the respective braces 71 and 80 for ease of the caregiver to monitor bedside.

It will thus be seen that a new and novel contact indicator for the therapeutic foot and ankle apparatus 12 has been illustrated and described and that various changes and modifications may be made therein without departing from the spirit and scope of the invention.

Therefore I claim:

1. A therapeutic ankle and foot apparatus comprising:
a leg portion, a foot portion and a heel portion, said foot portion being at an angle to said leg portion;
said heel portion being interconnected with said leg portion and said foot portion;
said heel portion having a configuration to provide a space between the patient's heel and said heel portion to prevent the application of pressure to the patient's heel; and
a contact sensor mechanism for sensing the patient's heel contacting said heel portion.

2. The therapeutic ankle and foot apparatus of claim 1 wherein said sensor mechanism further comprises, a contact switch communicating with an activation indicator, said contact switch attached to an interior side of said heel portion and said activation indicator located in a spaced relationship thereto.

3. The therapeutic ankle and foot apparatus of claim 2 wherein said activation indicator is visual.

4. The therapeutic ankle and foot apparatus of claim 2 wherein said activation indicator is audible.

5. The therapeutic ankle and foot apparatus of claim 2 wherein communication between said contact switch and said activation indicator is via wire.

6. The therapeutic ankle and foot apparatus of claim 2 wherein said contact switch further comprises:
a substantially flat base member having a plurality of longitudinally spaced recess areas therein, said recess areas having a contact wire traversing thereacross and communicating with lead wires, forming one side of an electrical circuit; and
a conductive mask attached to a non-conductive carrier strip substantially covering said base member, said conductive mask comprising a plurality of registration activation contact areas aligning over the respective recess areas in spaced relation thereto such that a plurality of deflectable contact switches is formed.

7. The therapeutic ankle and foot apparatus of claim 6, wherein said base member comprises a substantially non-conductive material.

8. The therapeutic ankle and foot apparatus of claim 2, wherein said sensor mechanism further comprises a proximal switch attached to said heel portion substantially adjacent to the patient's heel, said proximal switch communicating with said activation indicator via wire, said proximal switch working in conjunction with said contact switch for sensing the patient's heel contacting said heel portion.

9. The therapeutic ankle and foot apparatus of claim 2 wherein said heel portion is transversely flat and longitudinally contoured extending from said foot portion and engageable within said leg portion so as to provide the space between the patient's heel and said heel portion.

10. The therapeutic ankle and foot apparatus of claim 2 wherein said leg portion has a contoured leg support member with a recessed channel therein, said heel portion being secured within said recessed channel.

11. A therapeutic ankle and foot apparatus, comprising:
a leg portion, a foot portion and a heel portion, said foot portion being at an angle to said leg portion, said leg portion having a contoured leg support member;
said heel portion being interconnected with said foot portion, said heel portion being transversely flat and longitudinally contoured between said foot portion and said leg portion so as to provide a space between the patient's heel and said heel portion;
said foot portion having a recessed channel and said heel portion being secured within said recess channel, said foot portion comprising a footpad having side edges with at least one aperture tab, said footpad attached to an attachment base, and a walking pad being attached to said attachment base;

a foot engagement enclosure attached to said foot portion, said enclosure having a mounting base portion and a sleeve, said sleeve being secured to said mounting base portion through a strap extending from said aperture tab, said sleeve and durable mounting portion forming a pair of heel tabs, said heel tabs being secured over the patient's heel by a secondary strap; and a contact sensor mechanism for sensing when the patient's heel contacts said heel portion.

12. The therapeutic ankle and foot apparatus of claim 11 wherein said sensor mechanism further comprises a contact switch communicating with a transmitter and an activation indicator, said contact switch being attached to an interior side of said heel portion and said transmitter being attached to an outside surface of said ankle and foot apparatus.

13. The therapeutic ankle and foot apparatus of claim 12 wherein said activation indicator further comprise a receiver for receiving an output signal from said transmitter when the patient's heel contacts said contact switch, said activation indicator being located in spaced relation to said transmitter.

14. The therapeutic ankle and foot apparatus of claim 12 wherein said activation indicator further comprises a light indicator, said light being activated when the patient's heel contacts said contact switch.

15. The therapeutic ankle and foot apparatus of claim 12 wherein said activation indicator is audible.

16. A method for sensing incorrect positioning of a therapeutic ankle and foot apparatus comprising the steps of:

positioning a patient's leg and foot into said therapeutic ankle and foot apparatus, the therapeutic ankle and foot apparatus comprising a contact sensor mechanism, a leg portion, a foot portion and a heel portion, said foot portion being at an angle to said leg portion, said heel portion having a configuration to provide a space between the patient's heel and said heel portion to prevent the application of pressure to the patient's heel;

adjusting said ankle and foot apparatus to prevent the patient's heel from contacting said heel portion;

securing said ankle and foot apparatus to the patient's foot adjusted in said ankle and foot apparatus;

activating said sensor indicator mechanism when the patient's secured foot becomes incorrectly positioned; and readjusting said ankle and foot apparatus to prevent the incorrectly positioned patient's heel from contacting said heel portion.

17. The method of claim 16 wherein said sensor indicator mechanism further comprises a contact switch attached to said heel portion communicating with an activation indicator located in a spaced relationship thereto.

18. The method of claim 17, further comprising the step of activating an audio alarm when the patient's heel contacts said contact switch of said sensor indicator mechanism.

19. The method of claim 17 further comprising the step of activating an alarm light when the patient's heel contacts said contact switch of said sensor indicator mechanism.

20. A therapeutic leg apparatus comprising; a knee joint portion and an ankle joint portion, said knee joint portion being interconnected with said ankle portion, said knee portion having a configuration to provide a space between the patient's knee and said knee portion, a contact sensor for sensing the patient's knee contacting said knee portion of said therapeutic leg apparatus.

21. The therapeutic leg apparatus set forth in claim 20 wherein said sensor further comprises; a contact switch communicating with an alarm activation indicator located in spaced relation thereto.

22. The therapeutic leg apparatus set forth in claim 21 wherein said contact switch comprises; a substantially flat non-conductive base member having a plurality of longitudinally spaced recess areas therein, said recess areas having a contact surface transversing thereacross and communicating with lead wires forming one side of an electrical circuit; and a conductive mass attached to a non-conductive carrier strip substantially covering sand base member, said conductive mass comprising a plurality of registration activation contact areas aligning over the respective recess areas in spaced relation thereto such that a plurality of deflectable contact switches is formed.

23. The therapeutic leg apparatus of claim 21 wherein said sensor further comprises a proximal switch attached to said knee portion substantially adjacent to the patient's knee, said proximal switch communicating with said activation indicator via wire, said proximal switch working in conjunction with said contact switch for sensing the patient's knee contacting said knee portion.

24. A therapeutic anterior hyper-extension body brace apparatus having a sternum pad portion and a pubic pad portion, said sternum pad portion being interconnected with said pubic pad portion, said sternum pad portion engaging a patient, said sternum pad portion having an upper and lower perimeter edge portion, a contact sensor on said sternum pad for sensing a patient's contact with said upper perimeter edge portion.

25. A therapeutic body jacket brace comprising, a molded body enclosure members, said body enclosure members configured to provide spaces between the patient's body and said body enclosure members to prevent the application of pressure to the patient's selected body areas; and a plurality of contact sensors for sensing the patient's body contacting said body enclosure members.

26. The therapeutic body jacket brace set forth in claim 25 wherein said contact sensor further comprises; a contact switch communicating with an alarm activation indicator module located in spaced relation thereto.

27. The therapeutic body jacket brace set forth in claim 25 wherein said contact sensor further comprises a substantially flat base member having a plurality of longitudinally spaced recess areas therein, said recess areas having a contact wire traversing thereacross and communicating with lead wires, forming one side of an electrical circuit; and a conductive mask attached to a non-conductive carrier strip substantially covering said base member, said conductive mask comprising a plurality of registration activation contact areas aligning over the respective recess areas in spaced relation thereto, such that a plurality of deflectable contact switches is formed.

28. The therapeutic body jacket brace of claim 25 wherein said sensor further comprises a proximal switch attached to said body enclosure members substantially adjacent to the patient's body, said proximal switch communicating with said alarm activation indicator via wire, said proximal switch working in conjunction with said contact switch for sensing the patient's body contacting said body enclosure members.

29. The therapeutic anterior hyper-extension body brace set forth in claim 24 wherein said contact sensor further comprises; a contact switch communicating with an alarm activation indicator module located in spaced relation thereto.

30. The therapeutic anterior hyper extension body brace set forth in claim 24 wherein said contact sensor further comprises a substantially flat base member having a plurality of longitudinally spaced recess areas therein, said recess areas having a contact wire traversing thereacross and communicating with lead wires, forming one side of an electrical circuit; and a conductive mask attached to a non-conductive carrier strip substantially covering said base member, said conductive mask comprising a plurality of registration activation contact areas aligning over the respective recess areas in spaced relation thereto, such that a plurality of deflectable contact switches is formed.

31. The therapeutic anterior hyper-extension body brace set forth in claim 24 wherein said sensor further comprises a proximal switch attached to said body enclosure members substantially adjacent to the patient's body, said proximal switch communicating with said alarm activation indicator via wire, said proximal switch working in conjunction with said contact switch for sensing the patient's body contacting said body enclosure members.

\* \* \* \* \*